US 9,539,439 B2

(12) United States Patent
Jones et al.

(10) Patent No.: US 9,539,439 B2
(45) Date of Patent: Jan. 10, 2017

(54) APPARATUS FOR TREATING CELLULITE

(71) Applicant: Candela Corporation, Wayland, MA (US)

(72) Inventors: Christopher J. Jones, Leicester, MA (US); James C. Hsia, Weston, MA (US); Dilip Y. Paithankar, Wayland, MA (US)

(73) Assignee: Candela Corporation, Wayland, MA (US)

( * ) Notice: Subject to any disclaimer, the term of this patent is extended or adjusted under 35 U.S.C. 154(b) by 0 days.

(21) Appl. No.: 14/675,800

(22) Filed: Apr. 1, 2015

(65) Prior Publication Data

US 2015/0202460 A1    Jul. 23, 2015

Related U.S. Application Data

(62) Division of application No. 11/529,737, filed on Sep. 28, 2006, now Pat. No. 9,028,469.

(60) Provisional application No. 60/721,272, filed on Sep. 28, 2005.

(51) Int. Cl.
*A61N 5/06* (2006.01)
*A61B 18/20* (2006.01)
*A61B 17/00* (2006.01)
*A61B 18/00* (2006.01)
*A61B 18/18* (2006.01)
*A61N 5/00* (2006.01)
*A61N 5/067* (2006.01)

(52) U.S. Cl.
CPC ............ *A61N 5/0616* (2013.01); *A61B 18/203* (2013.01); *A61B 2017/00084* (2013.01); *A61B 2018/00005* (2013.01); *A61B 2018/00023* (2013.01); *A61B 2018/00029* (2013.01); *A61B 2018/00452* (2013.01); *A61B 2018/1807* (2013.01); *A61N 2005/007* (2013.01); *A61N 2005/063* (2013.01); *A61N 2005/067* (2013.01); *A61N 2005/0644* (2013.01); *A61N 2005/0659* (2013.01)

(58) Field of Classification Search
CPC ............ A61N 5/0616; A61N 2005/007; A61N 2005/063; A61N 2005/0644; A61N 2005/0659; A61N 2005/067; A61B 18/203; A61B 2017/00084; A61B 2018/00005; A61B 2018/00023; A61B 2018/00452; A61B 2018/1807
USPC ...................................................... 606/2–19
See application file for complete search history.

(56) References Cited

U.S. PATENT DOCUMENTS

| | | | |
|---|---|---|---|
| 6,219,584 B1 * | 4/2001 | Lee ..................... | A61M 1/3681 436/519 |
| 2003/0032950 A1 * | 2/2003 | Altshuler ............. | A61B 17/545 606/9 |
| 2004/0167501 A1 * | 8/2004 | Island .................. | A61B 18/203 606/9 |

* cited by examiner

*Primary Examiner* — Aaron Roane
(74) *Attorney, Agent, or Firm* — Manelli Selter PLLC; Edward J. Stemberger

(57) ABSTRACT

A treatment for subcutaneous fat and/or cellulite includes delivering a beam of radiation to a subcutaneous fat region disposed relative to a dermal interface in a target region of skin. The beam of radiation affects at least one fat cell in the subcutaneous fat region without causing substantial unwanted injury to the epidermal region and causes thermal injury to a dermal region to induce collagen formation to strengthen the target region of skin in a target region of skin. The treatment can include cooling an epidermal region of the target region of skin.

12 Claims, 8 Drawing Sheets

APPARATUS FOR TREATING CELLULITE

CROSS-REFERENCE TO RELATED APPLICATIONS

This application claims priority to and the benefit of U.S. provisional patent application Ser. No. 60/721,272 filed Sep. 28, 2005, the entire disclosure of which is herein incorporated by reference.

FIELD OF THE INVENTION

The invention relates generally to cosmetic treatments, and more particularly to using a beam of radiation to treat subcutaneous fat and strengthen dermal tissue to preclude subcutaneous fat from crossing a dermal interface and entering the dermal region.

BACKGROUND OF THE INVENTION

Cellulite is a common cosmetic problem of skin that appears as an irregularity of skin contour, and is often characterized by a dimpled or bumpy appearance of the skin. Cellulite commonly can be found around the thigh region, buttocks, arms, abdomen, and other regions of the body where large masses of fat can be found in close proximity to the skin surface.

Cellulite can result from fat permeating a dermal interface between a dermal layer and a subcutaneous fat layer of skin, which can be described as herniation of fat into the dermis. Typically, the dermis is weakened, as a result of stretching of the dermal tissue, tissue injury, or hormonal changes. A cellulite bump can result from subcutaneous fat that protrudes and/or permeates into the weakened dermis. A thinning of the dermal layer also can be associated with cellulite.

Cellulite can be treated by an invasive surgical procedure such as liposuction, but an invasive procedure can involve pain, can result in swelling and inflammation of tissue, and can require considerable recovery time. Massage can enhance circulation and lymphatic drainage, resulting in fluids being drained from the area, but massage only provides a temporary improvement in the condition. Repeated massage treatments can be required to maintain a cellulite-free appearance, and massage does not preclude new fat being formed from permeating into the dermal layer.

Treatments that include a massage component and irradiation of the tissue with light or ultrasonic energy have also been proposed to treat cellulite. These systems purport to break down the fat and promote its removal from the tissue, but they can not result in long-lasting benefits, since the normal fat regeneration process can result in the reappearance of cellulite as fatty tissue permeates into the dermal layer.

SUMMARY OF THE INVENTION

The technology, in various embodiments, features an apparatus for treating and a treatment for subcutaneous fat, such as cellulite. The treatment is not limited to cellulite and can be used for any fatty deposit located in or proximate to the dermal interface. Instead of being an invasive surgical procedure, treatment radiation is directed through the surface of the skin. Longer lasting benefits than prior art treatments can be achieved because, in one embodiment, a treatment, injures the fatty tissue and causes a thickening and/or strengthening of the dermis, which can prevent and/or preclude additional fatty tissue from permeating the dermal interface and/or from perturbing the dermal interface. In various embodiments, a treatment can, for example, reduce fat, remove a portion of fat, improve skin laxity, tighten skin, strengthen skin, thicken skin, induce new collagen formation, promote fibrosis of the dermal layer or subcutaneous fat layer, or be used for a combination of the aforementioned. Furthermore, a treatment can include a series of treatment cycles, so that fatty tissue can be reduced gradually, and/or the skin can be tightened gradually, resulting in a more cosmetically appealing appearance.

A treatment can include cooling to protect the skin surface, to minimize unwanted injury to the surface of the skin, and to minimize any pain that a patient may feel. An additional advantage of such a treatment is that the treatment can be performed with minimal acute cosmetic disturbance such that the patient can return to normal activity immediately after the treatment.

In one aspect, the technology features a method of treating a fatty deposit (e.g., cellulite) in a target region of skin. The method includes cooling an epidermal region of the target region of skin, and delivering a beam of radiation to a subcutaneous fat region disposed relative to a dermal interface in the target region of skin (a) to affect at least one fat cell in the subcutaneous fat region without causing substantial unwanted injury to the epidermal region, and (b) to cause thermal injury to a dermal region sufficient to induce collagen formation to strengthen and/or thicken the target region of skin. In various embodiments, the method can be used to strengthen and/or tighten the target region of skin to prevent subcutaneous fat from crossing the dermal interface into the dermal region and/or from perturbing the dermal interface. This can improve the appearance of a region of the body. In one embodiment, the treatment radiation is delivered to the target region in the absence of cooling.

In another aspect, the invention features an apparatus for treating cellulite in a target region of skin. The apparatus includes a source generating a beam of radiation, a delivery system coupled to the source, and a cooling system. The source includes a fiber coupled laser diode array. The delivery system directs the beam of radiation to a subcutaneous fat region disposed relative to a dermal interface in the target region of skin to affect at least one fat cell in the subcutaneous fat region and to cause thermal injury to a dermal region to induce collagen formation to strengthen the target region of skin. The cooling system cools an epidermal region of the target region to minimize substantial unwanted injury thereto.

In still another aspect, the invention features an apparatus for treating cellulite in a target region of skin. The apparatus includes means for cooling an epidermal region of the target region of skin and means for delivering a beam of radiation to a subcutaneous fat region disposed relative to a dermal interface in the target region of skin. The beam of radiation to affect at least one fat cell in the subcutaneous fat region without causing substantial unwanted injury to the epidermal region and to cause thermal injury to a dermal region to induce collagen formation to strengthen the target region of skin.

In yet another aspect, the invention features an apparatus including a source generating a beam of radiation and a housing enclosing the source. The housing includes an aperture to transmit the beam of radiation to a subcutaneous fat region disposed relative to a dermal interface in a target region of skin (a) to affect at least one fat cell in the subcutaneous fat region without causing substantial unwanted injury to the epidermal region, and (b) to cause thermal injury to a dermal region to induce collagen formation to strengthen the target region of skin. The source can include a fiber coupled laser diode array. The apparatus can include a cooling system for cooling an epidermal region of the target region to minimize substantial unwanted injury thereto.

In another aspect, the invention features a kit for improving the cosmetic appearance of a subcutaneous fat region disposed relative to a dermal interface in a target region of skin. The kit includes a source generating a beam of radiation and instruction means including instructions for directing the beam of radiation to the subcutaneous fat region. The beam of radiation affects at least one fat cell in the subcutaneous fat region without causing substantial unwanted injury to the epidermal region and causes thermal injury to a dermal region to induce collagen formation to strengthen the target region of skin. The source can include a fiber coupled laser diode array. The instruction means can control a cooling system for cooling an epidermal region of the target region to minimize substantial unwanted injury thereto. In certain embodiments, the instruction means can prescribe a wavelength, fluence, and pulse duration for treatment of the subcutaneous fat region.

In other examples, any of the aspects above, or any apparatus or method described herein, can include one or more of the following features. In various embodiments, the target region of skin can be strengthened to prevent subcutaneous fat from crossing the dermal interface into the dermal region. In certain embodiments, a fat cell can be damaged so that lipid contained within can escape and at least a portion of the lipid can be carried away from the target region. In some embodiments, a fat cell can be destroyed.

The beam of radiation can be delivered to the target region to thermally injure the at least one fat cell. In certain embodiments, collagen fibers in the dermal region can be partially denatured to strengthen and tighten the target region of skin. Sufficient thermal injury can cause an increase in extracellular matrix constituents for dermal skin rejuvenation. Fibroblasts can be activated to deposit increased amounts of collagen and extracellular matrix constituents in the target region. Thermal injury can induce fibrosis in at least one of the dermal layer, a subcutaneous fat region, at the dermal interface, and proximate to the dermal interface. In some embodiments, the beam of radiation can cause the temperature to peak at the dermal interface.

In various embodiments, the beam of radiation can have a wavelength between about 1,160 nm and 1,800 nm. In certain embodiments, the wavelength can be between about 1,190 nm and about 1,230 nm. In certain embodiments, the wavelength can be between about 1,700 nm and about 1,760 nm. The fluence can be between about 1 J/cm$^2$ and about 500 J/cm$^2$. In some embodiments, the fluence can be between about 10 J/cm$^2$ and about 150 J/cm$^2$. The pulse duration can be between about 0.1 second to 20 seconds. In certain embodiments, the beam of radiation can be delivered as a series of sub-pulses delivered over a time interval of between about 0.1 second to 20 seconds.

In various embodiments, the beam of radiation can be delivered to the target region about 0.5 mm to about 10 mm below the surface of the skin. In some embodiments, the beam of radiation can be delivered to the target region about 1 mm to about 10 mm below the surface of the skin. The target region of the skin can be between about 1 mm and about 5 mm below the surface of the skin.

In various embodiments, the target region of skin can be massaged before, during, or after irradiation of the target region of skin. Massaging can facilitate removal of the treated fatty tissue from the target region. In certain embodiments, the epidermal region of skin can be cooled at least one of before, during, and after delivering the beam of radiation to the interface of the dermal region and the subcutaneous fat region in the target region of skin. An osmotic agent can be applied to the target region of skin to reduce water content in the target region. A module can be used to apply the osmotic agent.

In certain embodiments, a focusing system can be used to focus the beam of radiation below the surface of the skin in the target region to affect the at least one fat cell. The focusing system can include a planoconvex lens and/or a plurality of lens to focus the beam of radiation. A vacuum system can draw the target region of skin against a concave contact surface of a lens to focus the beam of radiation to the at least one fat cell in the target region. The focusing system can direct the beam of radiation to the target region about 0.5 mm to about 5 mm below the exposed surface of the skin. In some embodiments, the fiber coupled laser diode array includes a high power semiconductor laser.

Other aspects and advantages of the invention will become apparent from the following drawings and description, all of which illustrate the principles of the invention, by way of example only.

BRIEF DESCRIPTION OF THE DRAWINGS

The advantages of the invention described above, together with further advantages, may be better understood by referring to the following description taken in conjunction with the accompanying drawings. The drawings are not necessarily to scale, emphasis instead generally being placed upon illustrating the principles of the invention.

DESCRIPTION OF THE INVENTION

Subcutaneous fat and/or cellulite can be treated by injuring fatty tissue (e.g., a fatty deposit located at or proximate to the dermal interface) and by thickening and/or strengthening of the dermis, which can prevent and/or preclude additional fatty tissue from perturbing the dermal interface. In various embodiments, a treatment can, for example, reduce fat, remove a portion of fat, improve skin laxity, tighten skin, strengthen skin, thicken skin, induce new collagen formation, promote fibrosis of the dermal layer or subcutaneous fat layer, or be used for a combination of the aforementioned.

Figure 1:
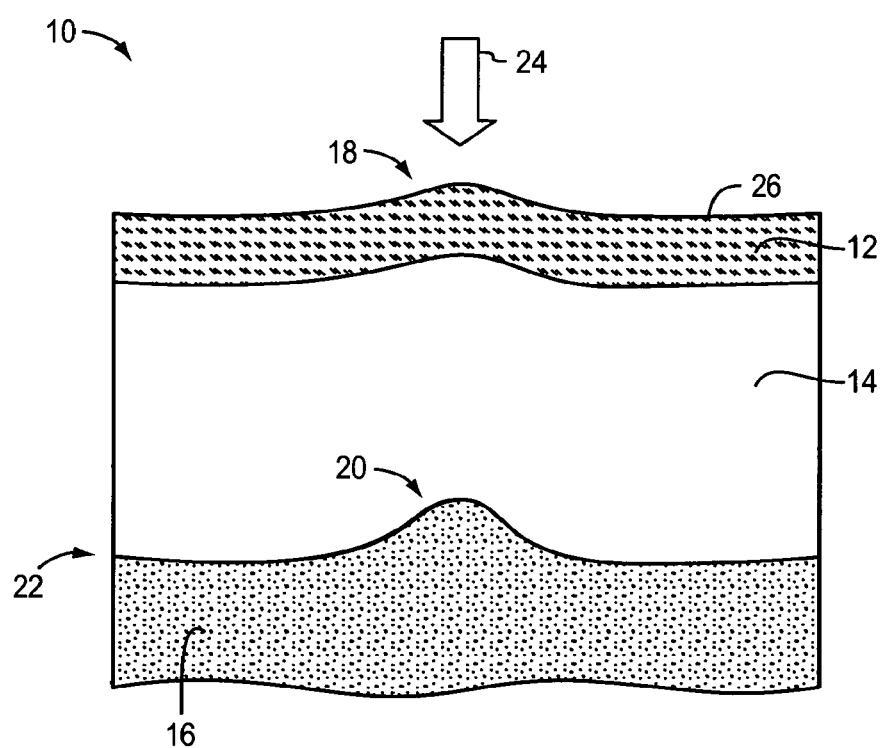
FIG. 1 shows a sectional view of skin including subcutaneous fat being treated by a beam of radiation.

FIG. 1 shows a cross-section of skin 10 including an epidermal layer 12, a dermal layer 14, and a layer of fatty tissue 16. A cellulite bump 18 is formed by a portion 20 of the fatty tissue 16 perturbing the dermal interface 22. The fatty tissue can push into and/or against the dermal interface 22. In some embodiments, a portion of the fatty tissue can permeate or cross the dermal interface 22 and invade the dermal layer 14. A beam of radiation 24 can be used to treat at least a portion of the fatty tissue 16 by delivery through a surface 26 of the epidermal layer 12. The radiation 24 penetrates through the epidermal layer 12 and the dermal layer 14 to treat at least a portion of the dermal layer 14.

The treatment radiation can damage one or more fat cells so that at least a portion of lipid contained within can escape or be drained from the treated region. At least a portion of the lipid can be carried away from the tissue through biological processes. In one embodiment, the body's lymphatic system can drain the treated fatty tissue from the treated region. In an embodiment where a fat cell is damaged, the fat cell can be viable after treatment. In one embodiment, the treatment radiation can destroy one or more fat cells. In one embodiment, a first portion of the fat cells is damaged and a second portion is destroyed. In one embodiment, a portion of the fat cells can be removed to selectively change the shape of the body region.

In some embodiments, the beam of radiation can be delivered to the target region to thermally injure, damage, and/or destroy one or more fat cells. For example, the beam of radiation can be delivered to a target chromophore in the target region. Suitable target chromophores include, but are not limited to, a fat cell, lipid contained within a fat cell, fatty tissue, a wall of a fat cell, water in a fat cell, and water in tissue surrounding a fat cell. The energy absorbed by the chromophore can be transferred to the fat cell to damage or destroy the fat cell. For example, thermal energy absorbed by dermal tissue can be transferred to the fatty tissue. In one embodiment, the beam of radiation is delivered to water within or in the vicinity of a fat cell in the target region to thermally injure the fat cell.

In various embodiments, treatment radiation can affect one or more fat cells and can cause sufficient thermal injury in the dermal region of the skin to elicit a healing response to cause the skin to remodel itself. This can result in more youthful looking skin and an improvement in the appearance of cellulite. In one embodiment, sufficient thermal injury induces fibrosis of the dermal layer, fibrosis on a subcutaneous fat region, or fibrosis in or proximate to the dermal interface. In one embodiment, the treatment radiation can partially denature collagen fibers in the target region. Partially denaturing collagen in the dermis can induce and/or accelerate collagen synthesis by fibroblasts. For example, causing selective thermal injury to the dermis can activate fibroblasts, which can deposit increased amounts of extracellular matrix constituents (e.g., collagen and glycosaminoglycans) that can, at least partially, rejuvenate the skin. The thermal injury caused by the radiation can be mild and only sufficient to elicit a healing response and cause the fibroblasts to produce new collagen. Excessive denaturation of collagen in the dermis causes prolonged edema, erythema, and potentially scarring. Inducing collagen formation in the target region can change and/or improve the appearance of the skin of the target region, as well as thicken the skin, tighten the skin, improve skin laxity, and/or reduce discoloration of the skin.

In various embodiments, a zone of thermal injury can be formed at or proximate to the dermal interface. Fatty tissue has a specific heat that is lower than that of surrounding tissue (fatty tissue, so as the target region of skin is irradiated, the temperature of the fatty tissue exceeds the temperature of overlying and/or surrounding dermal or epidermal tissue. For example, the fatty tissue has a volumetric specific heat of about 1.8 $J/cm^3$ K, whereas skin has a volumetric specific heat of about 4.3 $J/cm^3$ K. In one embodiment, the peak temperature of the tissue can be caused to form at or proximate to the dermal interface. For example, a predetermined wavelength, fluence, pulse duration, and cooling parameters can be selected to position the peak of the zone of thermal injury at or proximate to the dermal interface. This can result in collagen being formed at the bottom of the dermis and/or fibrosis at or proximate to the dermal interface. As a result, the dermal interface can be strengthened against fat herniation. For example, strengthening the dermis can result in long-term improvement of the appearance of the skin since new fat being formed or untreated fat proximate the dermal interface can be prevented and/or precluded from crossing the dermal interface into the dermis.

In one embodiment, fatty tissue is heated by absorption of radiation, and heat can be conducted into dermal tissue proximate the fatty tissue. The fatty tissue can be disposed in the dermal tissue and/or can be disposed proximate to the dermal interface. A portion of the dermal tissue (e.g., collagen) can be partially denatured or can suffer another form of thermal injury, and the dermal tissue can be thickened and/or be strengthened as a result of the resulting healing process. In such an embodiment, a fat-selective wavelength of radiation can be used.

In one embodiment, water in the dermal tissue is heated by absorption of radiation. The dermal tissue can have disposed therein fatty tissue and/or can be overlying fatty tissue. A portion of the dermal tissue (e.g., collagen) can be partially denatured or can suffer another form of thermal injury, and the dermal tissue can be thickened and/or be strengthened as a result of the resulting healing process. A portion of the heat can be transferred to the fatty tissue, which can be affected. In one embodiment, water in the fatty tissue absorbs radiation directly and the tissue is affected by heat. In such embodiments, a water selective wavelength of radiation can be used.

In various embodiments, a treatment can cause minimal cosmetic disturbance so that a patient can return to normal activity following a treatment. For example, a treatment can be performed without causing discernable side effects such as bruising, open wounds, burning, scarring, or swelling. Furthermore, because side effects are minimal, a patient can return to normal activity immediately after a treatment or within a matter of hours, if so desired.

Figure 2:
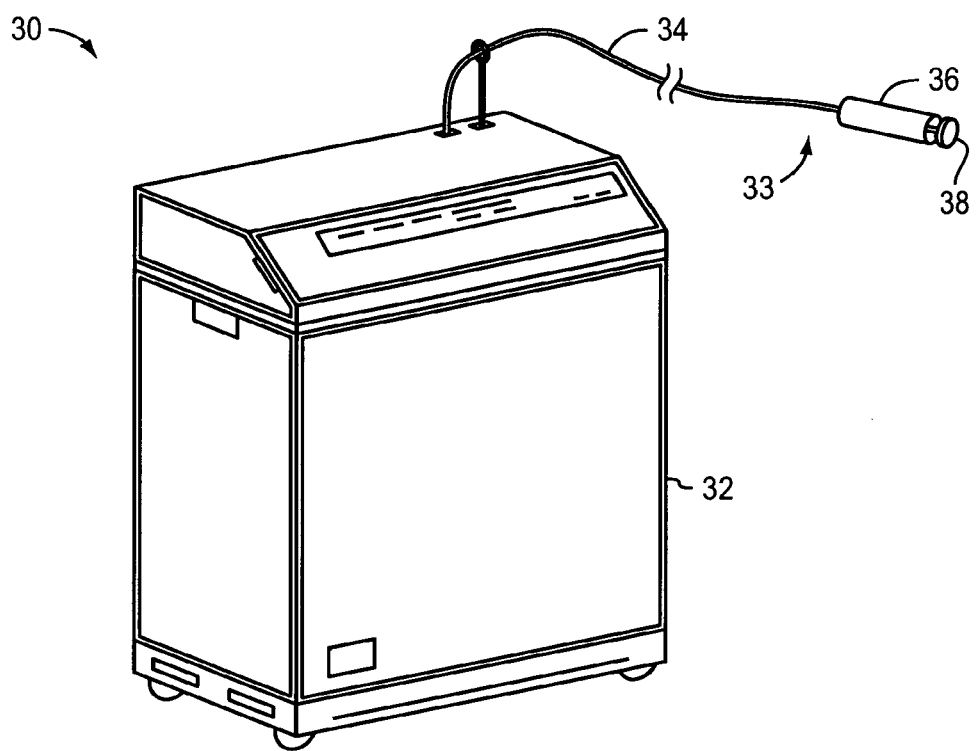
FIG. 2 shows an exemplary system for treating fatty tissue.

FIG. 2 shows an exemplary embodiment of a system 30 for treating tissue. The system 30 can be used to non-invasively deliver a beam of radiation to a target region. For example, the beam of radiation can be delivered through an external surface of skin over the target region. The system 30 includes an energy source 32 and a delivery system 33. In one embodiment, a beam of radiation provided by the energy source 32 is directed via the delivery system 33 to a target region. In the illustrated embodiment, the delivery system 33 includes a fiber 34 having a circular cross-section and a handpiece 36. A beam of radiation can be delivered by the fiber 34 to the handpiece 36, which can include an optical system (e.g., an optic or system of optics) to direct the beam of radiation to the target region. A user can hold or manipulate the handpiece 36 to irradiate the target region. The delivery system 13 can be positioned in contact with a skin surface, can be positioned adjacent a skin surface, can be positioned proximate a skin surface, can be positioned spaced from a skin surface, or a combination of the aforementioned. In the embodiment shown, the delivery system 33 includes a spacer 38 to space the delivery system 33 from the skin surface. In one embodiment, the spacer 38 can be a distance gauge, which can aid a practitioner with placement of the delivery system 33.

In various embodiments, the energy source 32 can be an incoherent light source, a coherent light source (e.g., a laser), a microwave generator, or a radio-frequency generator. In one embodiment, the source generates ultrasonic energy that is used to treat the tissue. In some embodiments, two or more sources can be used together to effect a treatment. For example, an incoherent source can be used to provide a first beam of radiation while a coherent source provides a second beam of radiation. The first and second beams of radiation can share a common wavelength or can have different wavelengths. In an embodiment using an incoherent light source or a coherent light source, the beam of radiation can be a pulsed beam, a scanned beam, or a gated continuous wave (CW) beam. In one embodiment, the source includes an ultrasonic energy device to disrupt or destroy fat cells and a radiation source to induce collagen formation or improve skin laxity.

In various embodiments, the beam of radiation can have a wavelength between about 1000 nm and about 2,600 nm, although longer and shorter wavelengths can be used depending on the application. In some embodiments, the wavelength can be between about 1,000 nm and about 2,200 nm. In other embodiments, the wavelength can be between about 1,160 nm and about 1,800 nm. In yet other embodiments, the wavelength can be between about 1,190 nm and about 1,230 nm or between about 1,700 nm and about 1,760 nm. In one embodiment, the wavelength is about 1,210 nm or about 1,720 nm. In one detailed embodiment, the wavelength is about 1,208 nm, 1,270 nm, 1,310 nm, 1,450 nm, 1,550 nm, 1,720 nm, 1,930 nm, or 2,100 nm. One or more of the wavelengths used can be within a range of wavelengths that can be transmitted to fatty tissue and absorbed by the fatty tissue in the target region of skin.

In various embodiments, the beam of radiation can have a fluence between about 1 J/cm$^2$ and about 500 J/cm$^2$, although higher and lower fluences can be used depending on the application. In some embodiments, the fluence can be between about 10 J/cm$^2$ and about 150 J/cm$^2$. In one embodiment, the fluence is between about 5 J/cm$^2$ and about 100 J/cm$^2$.

In various embodiments, the beam of radiation can have a spotsize between about 0.5 mm and about 25 mm, although larger and smaller spotsizes can be used depending on the application.

In various embodiments, the beam of radiation can have a pulse duration between about 10 μs and about 30 s, although larger and smaller pulse durations can be used depending on the application. In one embodiment, the beam of radiation can have a pulse duration between about 0.1 second and about 20 seconds. In one embodiment, the beam of radiation can have a pulse duration between about 1 second and 20 seconds. In certain embodiments, the beam of radiation can be delivered in a series of sub-pulses spaced in time such that within a region of tissue, the tissue is exposed to radiation intermittently over total time interval of between about 0.1 second and about 20 seconds.

In various embodiments, the beam of radiation can be delivered at a rate of between about 0.1 pulse per second and about 10 pulses per second, although faster and slower pulse rates can be used depending on the application.

In various embodiments, the parameters of the radiation can be selected to deliver the beam of radiation to a predetermined depth. In some embodiments, the beam of radiation can be delivered to the target region about 0.5 mm to about 10 mm below an exposed surface of the skin, although shallower or deeper depths can be selected depending on the application. In one embodiment, the beam of radiation is delivered to the target region about 1 mm to about 10 mm below an exposed surface of the skin.

In various embodiments, the tissue can be heated to a temperature of between about 50° C. and about 80° C., although higher and lower temperatures can be used depending on the application. In one embodiment, the temperature is between about 55° C. and about 70° C.

To minimize unwanted thermal injury to tissue not targeted (e.g., an exposed surface of the target region and/or the epidermal layer), the delivery system 33 shown in FIG. 2 can include a cooling system for cooling before, during or after delivery of radiation, or a combination of the aforementioned. Cooling can include contact conduction cooling, evaporative spray cooling, convective air flow cooling, or a combination of the aforementioned. In one embodiment, the handpiece 36 includes a skin contacting portion that can be brought into contact with the skin. The skin contacting portion can include a sapphire or glass window and a fluid passage containing a cooling fluid. The cooling fluid can be a fluorocarbon type cooling fluid, which can be transparent to the radiation used. The cooling fluid can circulate through the fluid passage and past the window to cool the skin.

A spray cooling device can use cryogen, water, or air as a coolant. In one embodiment, a dynamic cooling device can be used to cool the skin (e.g., a DCD available from Candela Corporation). For example, the delivery system 33 shown in FIG. 2 can include tubing for delivering a cooling fluid to the handpiece 36. The tubing can be connected to a container of a low boiling point fluid, and the handpiece can include a valve for delivering a spurt of the fluid to the skin. Heat can be extracted from the skin by virtue of evaporative cooling of the low boiling point fluid. The fluid can be a non-toxic substance with high vapor pressure at normal body temperature, such as a Freon, tetrafluoroethane, or liquefied $CO_2$.

The time duration of cooling and of radiation application can be adjusted to maximize heating and thermal injury to the region proximate to the dermal interface. In tissue where the dermal interface is deeply situated, the cooling time can be lengthened such that cooling can be extended deeper into the skin. At the same time, the time duration of radiation application can be lengthened such that heat generated by the radiation in the region of dermis closer to the skin surface can be removed via thermal conduction and blood flow, thereby minimizing injury to the tissue overlying the dermal interface. Similarly if the dermis overlying the dermal interface is thin, the time duration of cooling and of radiation application can be adjusted to be shorter, such that thermal injury is confined to the region proximate to the dermal interface.

In various embodiments, a topical osmotic agent is applied to the region of skin to be treated, prior to treatment. The osmotic agent reduces the water content in the dermis overlying the dermal interface. This reduction in the water content can increase the transmission of the radiation into the dermal interface region and into the subcutaneous fat, thereby more effectively treating the area, reducing injury to the dermis, and reducing treatment pain. The osmotic agent can be glycerin or glycerol. A module can be used to apply the osmotic agent. The module can be a needle or syringe. The module can include a reservoir for retaining the osmotic agent and an injector for applying the agent to a skin region.

In various embodiments, a delivery system can include a focusing system for focusing the beam of radiation below the surface of the skin in the target region to affect at least one fat cell. The focusing system can direct the beam of radiation to the target region about 0.1 mm to about 10 mm below the exposed surface of the skin. In some embodiments, the delivery system can include a lens, a planoconvex lens, or a plurality of lens to focus the beam of radiation.

Figure 3:
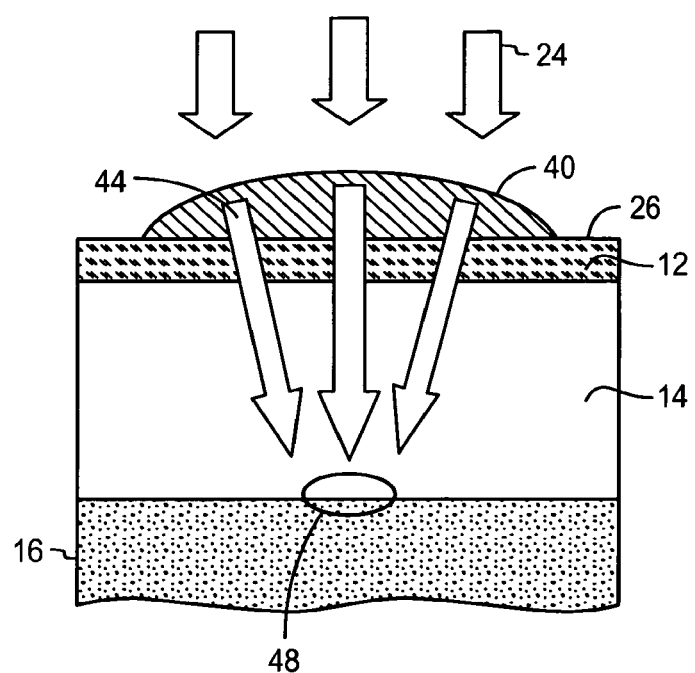
FIG. 3 depicts a planoconvex lens positioned on a skin surface.

FIG. 3 shows a planoconvex lens 40 positioned on a surface 26 of a section of skin, including an epidermal region 12, a dermal region 14, and a layer of fatty tissue 16. The planoconvex lens 40 focuses radiation 24 (focusing shown by arrows 44) to a sub surface focal region 48, which can include at least one fat cell. In certain embodiments, the element contacting the skin can be pressed into or against the skin to displace blood in the dermis, thereby increasing the transmission of the radiation through the dermis and reducing unwanted injury to the skin.

Figure 4:
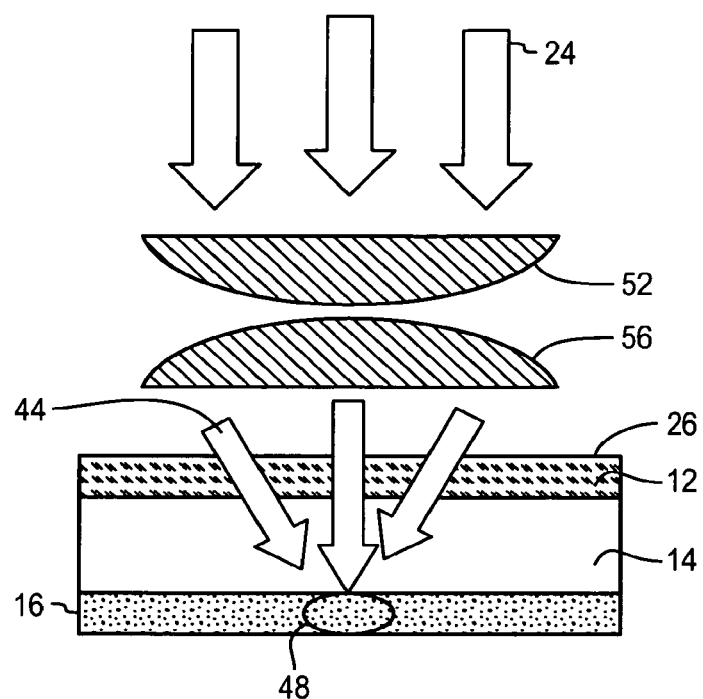
FIG. 4 shows a plurality of lens focusing radiation to a target region of skin.

FIG. 4 shows a plurality of lens 52, 56 spaced from the skin surface 26. The plurality of lens 52, 56 focus the radiation 24 (focusing shown by the arrows 44) to the sub surface focal region 48.

Figure 5:
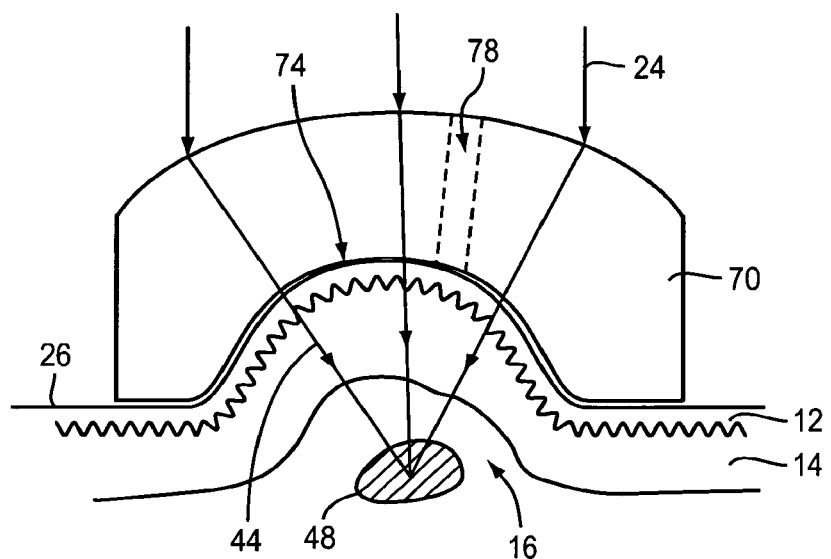
FIG. 5 shows a lens having a concave surface positioned on a skin surface.

FIG. 5 shows a lens 70 having a concave surface 74 for contacting the skin surface 26. In certain embodiments, the lens 70 is placed proximate to a target region of skin. Vacuum can be applied to draw the target region of skin against the concave surface 74 of the lens 70. Vacuum can be applied through orifice 78 in the lens 70 by a vacuum device. The lens 70 focuses the radiation 24 to the sub surface focal region 48.

In various embodiments, the source of radiation can be a diode laser having sufficient power to affect one or more fat cells. An advantage of diode lasers is that they can be fabricated at specific wavelengths that target fatty tissue. A limitation, though, of many diode laser devices and solid state devices targeting fatty tissue is the inability to produce sufficient power to effectuate a successful treatment.

In one embodiment, a diode laser of the invention is a high powered semiconductor laser. In one embodiment, the source of radiation is a fiber coupled diode laser array. For example, an optical source of radiation can include a plurality of light sources (e.g., semiconductor laser diodes) each adapted to emit a beam of light from a surface thereof. A plurality of first optical fibers each can have one end thereof adjacent the light emitting surface of a separate one of the light sources so as to receive the beam of light emitted therefrom. The other ends of the first optical fibers can be bundled together in closely spaced relation so as to effectively emit a single beam of light, which is a combination of the beams from all of the first optical fibers. A second optical fiber can have an end adjacent the other ends of the first optical fibers to receive the beam of light emitted from the bundle of first optical fibers. The beam of light from the bundled other ends of the first optical fibers can be directed into the second optical fiber. The first optical fiber can have a numerical aperture less than that of the second fiber. An exemplary fiber coupled diode laser array is described in U.S. Pat. No. 5,394,492, owned by the assignee of the instant application and the entire disclosure of which is herein incorporated by reference.

In various embodiments, beams from multiple diode lasers or diode laser bars can be combined using one or more lens. In one embodiment, an array of diode lasers is mounted in a handpiece of the delivery system, and respective beams of radiation from each diode laser can be directed to the target region. The beams of radiation can be combined so that they are incident at substantially the same point. In one embodiment, the one or more lens direct the multiple beams of radiation into a single optical fiber. A handpiece of the delivery system projects the combined beam of radiation to the target region of skin.

In various embodiments, a laser diode array can include a plurality of discrete emitter sections mounted on a substrate, e.g., a laser bar. Each discrete emitter section can include a light emitting material having an active region and an inactive region. Each discrete emitter section can be a laser diode. The substrate provides electrical isolation between adjacent discrete emitter sections. A plurality of wire bonds can connect electrically the plurality of discrete emitter sections in a series configuration. Each discrete emitter section can be physically isolated from an adjacent discrete emitter section by, for example, mechanically dicing to remove a portion of the inactive region. In various embodiments, the light emitting material is a semiconductor material. Suitable semiconductor materials include InGaAlP, InGaP, InGaAs, InGaN, or InGaAsP. In one embodiment, the active region is InGaAs, and the inactive region is GaAs. In various embodiments, the substrate can be diamond, ceramic, BeO, alumina, or a gold plated ceramic. The light emitting material can be soldered to the substrate, e.g., using tin-containing solders such as SnBi, SnPb, and SnPbAg (e.g., Sn62) and gold-containing solders such as AuGe. An exemplary laser diode array is described in U.S. patent application Ser. No. 11/503,492 file Aug. 11, 2006, owned by the assignee of the instant application and the entire disclosure of which is herein incorporated by reference.

Figures 6A, 6B:
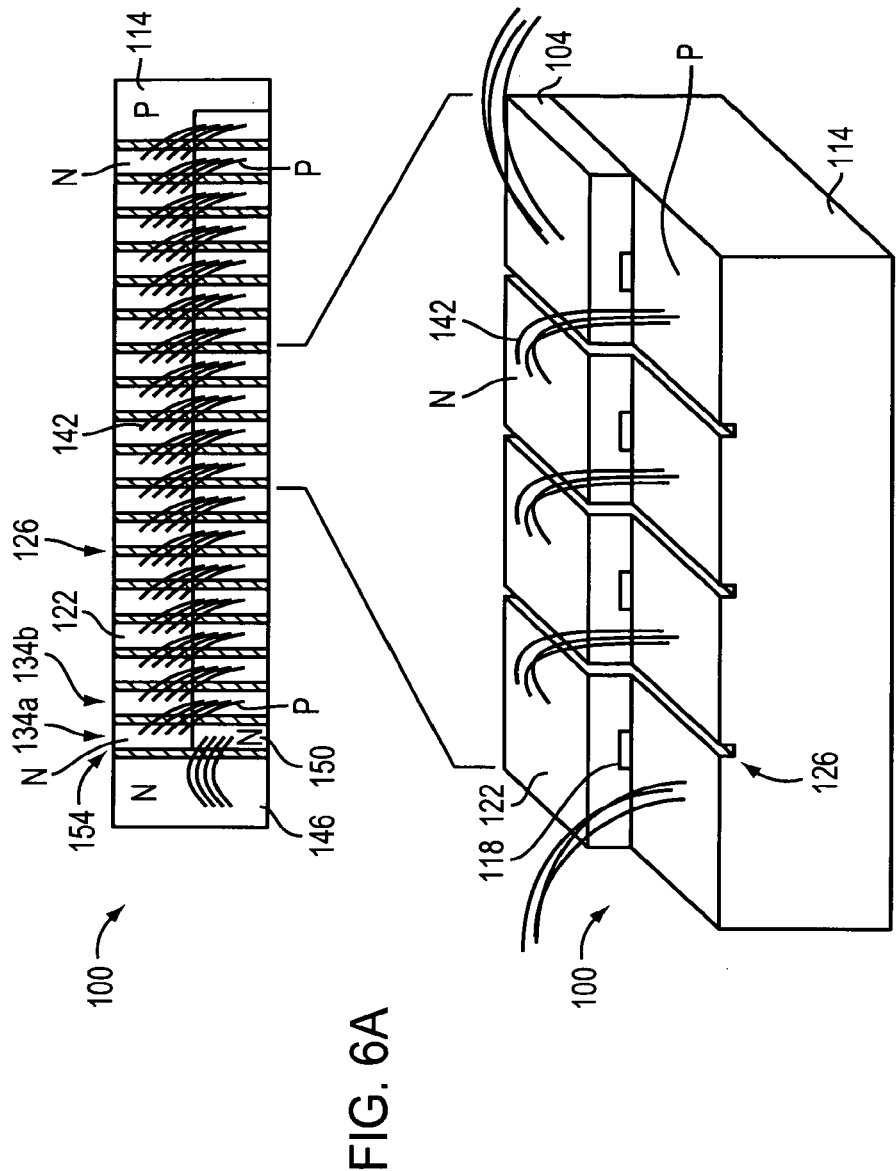
FIG. 6A shows a plan view of a laser diode array.
FIG. 6B shows an enlarged perspective view of the laser diode array of FIG. 6A.

FIGS. 6A and 6B shows a laser diode array 100 including a light emitting material 104 formed on a substrate 114. The light emitting material 104 includes one or more active regions 118 and an inactive region 122. Cuts 126 can be positioned between adjacent active regions 118 to form a plurality of discrete emitter sections 134. Cuts 126 can be removal points or dicing points. Each discrete emitter section 134 can be electrically and/or physically isolated from an adjacent discrete emitter section. FIG. 6B shows a first n-type region 146 connected to a second n-type region 150 over an isolation cut 154 so that an operator can have a soldering point for connecting to a drive circuit. The remaining connections are formed between an n-type region and an adjacent p-type region. For example, a n-type region of a first discrete emitter section 134a of the light emitting material 104 can be electrically coupled to a p-type region of a second discrete emitter section 134b. The p-type region can be electrically coupled to a portion of the substrate 114, and the n-type region of the first discrete emitter section 134a can be connected to that substrate 114 portion. For example, FIG. 6B shows an enlarged view of four discrete emitter sections 134 of the laser diode array 100 where the wire 142 is bonded to the substrate 114.

In certain embodiments, a p-type region of a first discrete emitter section 134 of the light emitting material 104 can be electrically coupled to a n-type region of a second discrete emitter section 134. The n-type region can be electrically coupled to a portion of the substrate 114, and the p-type region of the first discrete emitter section 134 can be connected to that substrate 114 portion.

Figure 7:
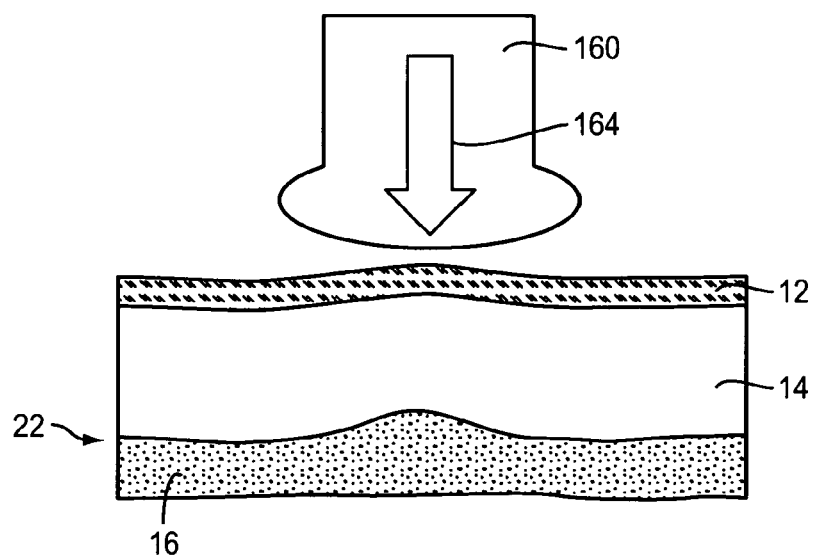
FIG. 7 shows a handpiece of an ultrasound device placed proximate to a skin surface.

In various embodiments, an ultrasound device can be used to measure the depth or position of the fatty tissue. For example, a high frequency ultrasound device can be used. FIG. 7 shows a handpiece of an ultrasound device 160 placed proximate to the skin to make a measurement. In one embodiment, the ultrasound device 160 can be place in contact with the skin surface. The ultrasound device 160 can deliver ultrasonic energy 164 to measure position of the dermal interface 22, so that radiation can be directed to the interface 22, as shown, e.g., in FIGS. 1, 3-5, and 8.

The time duration of the cooling and of the radiation application can be adjusted so as to maximize the thermal injury to the vicinity of the dermal interface 22. For example, if the position of the fatty tissue is known, then parameters of the optical radiation, such as pulse duration and/or fluence, can be optimized for a particular treatment. Cooling parameters, such as cooling time and/or delay between a cooling and irradiation, can also be optimized for a particular treatment. Accordingly, a zone of thermal treatment can be predetermined and/or controlled based on parameters selected. For example, the zone of thermal injury can be positioned in or proximate to the dermal interface.

Figure 8:
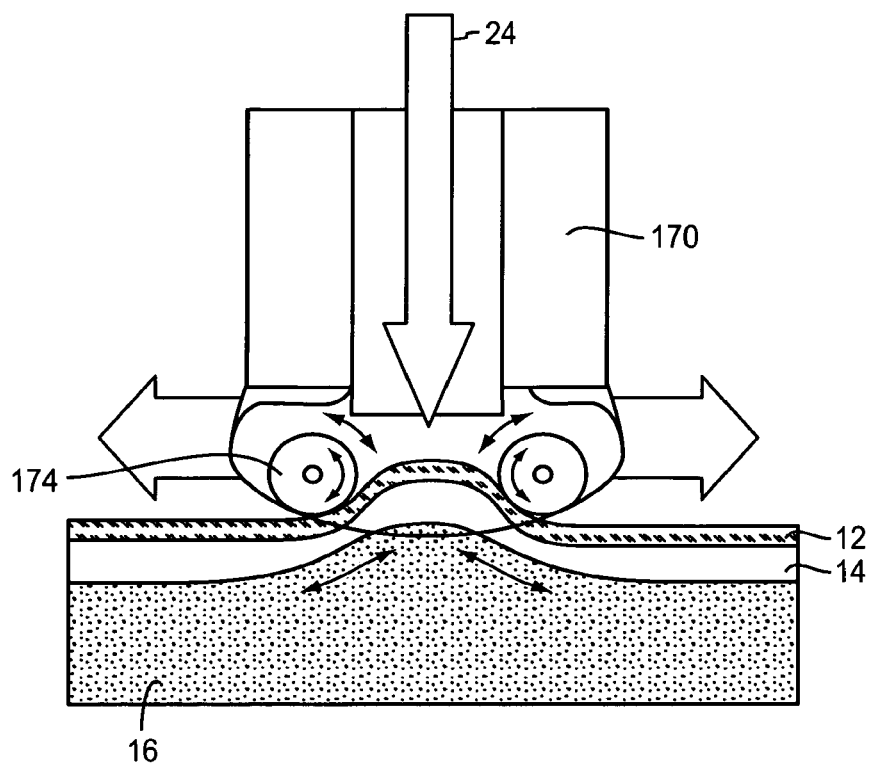
FIG. 8 depicts a handpiece used to massage the skin.

In various embodiments, the target region of skin can be massaged before, during, and/or after irradiation of the target region of skin. The massage can be a mechanical massage or can be manual massage. FIG. 8 depicts a handpiece 170 that includes rollers 174 to massage the skin. Radiation 24 can be delivered through a central portion of the handpiece 170. The massage handpiece 170 can be adapted to fit over the delivery system 13 shown in FIG. 2. In one embodiment, a delivery system can be formed with a mechanical massage device affixed. In one embodiment, vacuum can be used to pull the tissue into the device, which can provide an additional massage effect. In one embodiment, a person massages the target region of skin after irradiation of the tissue. Massaging the target region of skin can facilitate removal of the treated fatty tissue from the target region. For example, massaging can facilitate draining of the treated fatty tissue from the treated region.

The invention features a kit suitable for use in the treatment of subcutaneous fat and/or cellulite. The kit can be used to improve the cosmetic appearance of a region of skin. The kit can include a source of a beam of radiation and instruction means. The instruction means can include instructions for directing the beam of radiation to a subcutaneous fat region. The beam of radiation can affect at least one fat cell in the subcutaneous fat region without causing substantial unwanted injury to the epidermal region and cause thermal injury to a dermal region to induce collagen formation to strengthen the target region of skin. The source can include a fiber coupled laser diode array. A cooling system can be used to cool an epidermal region of the target region to minimize substantial unwanted injury thereto. The instruction means can prescribe a wavelength, fluence, and/or pulse duration for treatment of the subcutaneous fat region. The instruction means, e.g., treatment guidelines, can be provided in paper form, for example, as a leaflet, booklet, book, manual, or other like, or in electronic form, e.g., as a file recorded on a computer readable medium such as a drive, CD-ROM, DVD, or the like.

In some embodiments, the instruction means can be implemented in digital electronic circuitry, or in computer hardware, firmware, software, or in combinations of them. The implementation can be as a computer program product, i.e., a computer program tangibly embodied in an information carrier, e.g., in a machine-readable storage device or in a propagated signal, for execution by, or to control the operation of, data processing apparatus, e.g., a programmable processor, a computer, or multiple computers. A computer program can be written in any form of programming language, including compiled or interpreted languages, and the computer program can be deployed in any form, including as a stand-alone program or as a subroutine, element, or other unit suitable for use in a computing environment. A computer program can be deployed to be executed on one computer or on multiple computers at one site.

The instruction means can be performed by one or more programmable processors executing a computer program to perform functions of the technology by operating on input data and generating output. The instruction means can also be performed by, and an apparatus can be implemented as, special purpose logic circuitry, e.g., an FPGA (field programmable gate array) or an ASIC (application-specific integrated circuit). Subroutines can refer to portions of the computer program and/or the processor/special circuitry that implements that functionality.

Processors suitable for the execution of a computer program include, by way of example, both general and special purpose microprocessors, and any one or more processors of any kind of digital computer. Generally, a processor receives instructions and data from a read-only memory or a random access memory or both. The essential elements of a computer are a processor for executing instructions and one or more memory devices for storing instructions and data. Generally, a computer also includes, or be operatively coupled to receive data from or transfer data to, or both, one or more mass storage devices for storing data, e.g., magnetic, magneto-optical disks, or optical disks. Data transmission and instructions can also occur over a communications network. Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in special purpose logic circuitry.

To provide for interaction with a user, the above described techniques can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer (e.g., interact with a user interface element). Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The above described techniques can be implemented in a distributed computing system that includes a back-end component, e.g., as a data server, and/or a middleware component, e.g., an application server, and/or a front-end component, e.g., a client computer having a graphical user interface and/or a Web browser through which a user can interact with an example implementation, or any combination of such back-end, middleware, or front-end components. The components of the system can be interconnected by any form or medium of digital data communication, e.g., a communication network. Examples of communication networks include a local area network ("LAN") and a wide area network ("WAN"), e.g., the Internet, and include both wired and wireless networks.

The computing system can include clients and servers. A client and a server are generally remote from each other and typically interact through a communication network. The relationship of client and server arises by virtue of computer programs running on the respective computers and having a client-server relationship to each other.

While the technology has been particularly shown and described with reference to specific illustrative embodiments, it should be understood that various changes in form and detail may be made without departing from the spirit and scope of the technology.

What is claimed:

1. An apparatus for treating cellulite in a target region of skin, comprising:
a source generating a beam of radiation, the source including a fiber coupled laser diode array including a plurality of discrete emitter sections mounted on a substrate;
a delivery system coupled to the source for generating a beam of radiation and including at least a handpiece to direct the beam of radiation to a target region of skin and a spacer to space the delivery system from skin surface,
wherein the handpiece also includes a high frequency ultrasound device constructed and arranged to be placed in contact with the skin surface to measure position of a dermal-subcutaneous interface, so that the beam of radiation is directed to the dermal-subcutaneous interface, and
a focusing system to focus the beam of radiation below the surface of the skin in the target region of skin and wherein a focusing system element is constructed and arranged to contact the skin and be pressed into or against the skin to displace blood in dermis and increase transmission of the beam of radiation through the dermis to reduce unwanted injury to the skin,
wherein the focusing system comprises a planoconvex lens to direct and focus the beam of radiation to the target region of skin 0.5 mm to 5 mm below an exposed surface of skin.

2. The apparatus of claim 1, wherein the source generating the beam of radiation is constructed and arranged to generate radiation that has a wavelength of 1,160 nm to 1,800 nm, a fluence of 10 J/cm$^2$ to 150 J/cm$^2$, and a pulse duration of 0.1 second to 20 seconds.

3. The apparatus of claim 1, wherein the fiber coupled laser diode array is constructed and arranged to generate a beam of radiation having a wavelength between 1,190 nm and 1,230 nm.

4. The apparatus of claim 1, wherein the source generating the beam of radiation delivers the radiation to the target region of skin as a series of sub-pulses spaced in time such that the target region of skin is exposed to the beam of radiation over a time interval of 0.1 second to 20 seconds.

5. The apparatus of claim 1, wherein the fiber coupled laser diode array that comprises a high power semiconductor laser.

6. The apparatus of claim 1, wherein the delivery system further comprises rollers to massage the skin at least one of before, during, and after irradiation of the target region of skin.

7. The apparatus of claim 1, wherein the cooling system is constructed and arranged to cool an epidermal and superficial dermal regions of skin at least one of before, during, and after delivering the beam of radiation.

8. The apparatus of claim 1, wherein the delivery system is constructed and arranged to direct the beam of radiation to the target region of skin to strengthen the target region of skin to prevent subcutaneous fat from crossing a dermal interface into the dermal region.

9. The apparatus of claim 1, wherein the delivery system is constructed and arranged to direct a beam of radiation to a target region of skin to:
(i) partially denature collagen fibers in the dermal region to strengthen and tighten a target region of skin; or
(ii) cause sufficient thermal injury to increase extracellular matrix constituents for dermal skin rejuvenation; or
(iii) activate fibroblasts which deposit increased amounts of collagen and extracellular matrix constituents in the target region; or
(iv) cause thermal injury to induce fibrosis in at least one of the dermal layer, a subcutaneous fat region, at the dermal-subcutaneous interface, and proximate to the dermal-subcutaneous interface.

10. The apparatus of claim 1, further comprising a module configured to apply an osmotic agent to the target region of skin to reduce water content and increase transmission of a beam of radiation into dermal-subcutaneous interface region in the target region of skin.

11. The apparatus of claim 1, further comprising:
a housing enclosing the source, the housing including an aperture to transmit the beam of radiation to the target region of skin.

12. An apparatus for treating cellulite in a target region of skin, comprising:
a source generating a beam of radiation, the source including a fiber coupled laser diode array including a plurality of discrete emitter sections mounted on a substrate;
a delivery system coupled to the source for generating a beam of radiation and including at least a handpiece to direct the beam of radiation to a target region of skin and a spacer to space the delivery system from skin surface,
wherein the handpiece also includes a high frequency ultrasound device constructed and arranged to be placed in contact with the skin surface to measure position of a dermal-subcutaneous interface, so that the beam of radiation is directed to the dermal-subcutaneous interface, and
a focusing system to focus the beam of radiation below the surface of the skin in the target region of skin and,
a vacuum system and wherein the focusing system comprises a lens with a concave contact surface and an orifice in the lens communicating with the vacuum system.

* * * * *